United States Patent [19]

Cook, Jr.

[11] 4,225,518
[45] Sep. 30, 1980

[54] PURIFICATION OF META-CHLORONITROBENZENE

[75] Inventor: James A. Cook, Jr., Barberton, Ohio

[73] Assignee: PPG Industries, Inc., Pittsburgh, Pa.

[21] Appl. No.: 965,805

[22] Filed: Dec. 4, 1978

[51] Int. Cl.$^2$ .............................................. C07C 79/12
[52] U.S. Cl. ................................. 568/937; 260/705; 260/707
[58] Field of Search ........................ 260/646, 705, 707

[56] References Cited

U.S. PATENT DOCUMENTS

| | | | |
|---|---|---|---|
| 2,245,945 | 6/1941 | Van Dijck et al. | 260/575 |
| 2,795,620 | 6/1957 | Bloom et al. | 260/646 |
| 2,795,621 | 6/1957 | Bloom et al. | 260/646 |
| 3,051,650 | 8/1962 | Pfennig | 208/338 |
| 3,311,666 | 3/1967 | Dunn | 260/646 |
| 3,816,551 | 6/1974 | Lee | 260/646 |
| 4,102,753 | 7/1978 | Stephenson | 260/646 X |

OTHER PUBLICATIONS

Kryuger et al., vol. 28, p. 1593 (1934).
Urbanski, Chemistry and Technology of Explosives, vol. 1, The MacMillan Co., New York, 1964, pp. 456 to 458.

*Primary Examiner*—Leland A. Sebastian
*Attorney, Agent, or Firm*—Irwin M. Stein

[57] ABSTRACT

This invention relates to the treatment of an isomeric mixture of chloronitrobenzenes to provide a product higher in meta-chloronitrobenzene content, and lower in ortho-chloronitrobenzene and para-chloronitrobenzene content. In particular, a liquid mixtuure of ortho-, meta-, and para-chloronitrobenzene isomers containing a major amount of the meta isomer is solidified by dispersing the isomeric mixture in a partially miscible solvent at temperatures below the melting point of meta-chloronitrobenzene, the solvent and its temperature being selected so that the chloronitrobenzene isomers are sparingly soluble in the solvent. More particularly, a liquid isomeric mixture of ortho-, meta- and para-chloronitrobenzene containing a major amount of meta-chloronitrobenzene is dispersed in a lower alkylene glycol solvent that is at a temperature below the melting point of meta-chloronitrobenzene. A finely divided solid is collected, for example, by filtration, to provide a product enriched in meta-chloronitrobenzene.

9 Claims, No Drawings

PURIFICATION OF META-CHLORONITROBENZENE

BACKGROUND OF THE INVENTION

The chlorination of nitrobenzene produces an isomeric mixture containing the meta isomer as the major chloronitrobenzene constituent. It is believed that other methods of producing chloronitrobenzene, such as the nitration of chlorobenzene, produce products in which the distribution of the ortho, meta, and para isomers differ from that obtained by the chlorination of nitrobenzene.

The separation of mixtures of chloronitrobenzene isomers, into pure or substantially pure fractions is known to present problems in that many of the procedures are yield limited and/or involve a series of complex process steps. There is interest by the chemical industry in economically obtaining the meta isomer of chloronitrobenzene in substantially pure form for use as a chemical intermediate in various processes. The simple high yield process disclosed herein for accomplishing that object is of particular interest for that reason.

Among the procedures for separating mixtures of chloronitrobenzene isomers described in the art are the following:

U.S. Pat. No. 3,311,666, to Dunn, relates to the separation of chloronitrobenzene isomers by crystallization and fractionation and discusses the difficulties encountered in distillation and crystallization techniques.

U.S. Pat. No. 3,816,551, to Lee, relates to the use of crystallization in separating isomers of chloronitrobenzene. Specifically, the para isomer is separated employing continuous crystallization in the presence of water.

U.S. Pat. No. 2,795,620 and U.S. Pat. No. 2,795,621 to Bloom et al, discuss various methods for the manufacture of meta-chloronitrobenzene and problems related to chloronitrobenzene isomer separation. The patents are specifically directed to separating ortho- and para-chloronitrobenzene from meta-chloronitrobenzene by means of a sulfonation Process.

U.S. Pat.No. 2,245,945, to van Dijck et al, relates to a process for the separation of isomeric organic compounds, including mixtures of ortho- and para-chloronitrobenzene, by the use of two selective solvents partially immiscible with one another to cause distribution of the isomers between the solvents.

U.S. Pat. No. 3,051,650, to Pfennig relates to separating chemical compounds using solvents and liquified sulfur dioxide.

DESCRIPTION OF THE INVENTION

The present invention relates to a process for enriching the meta-chloronitrobenzene content of a chloronitrobenzene isomer mixture containing principally meta-chloronitrobenzene by solidifying a mixture of the chloronitrobenzene isomers in the presence of a partially miscible solvent. More specifically, the invention comprises dispersing a liquid (e.g., molten) mixture of chloronitrobenzene isomers containing meta-chloronitrobenzene as the major constitutuent in a partially miscible liquid solvent that is at a temperature below the melting point of meta-chloronitrobenzene, the solvent and temperature being selected so that the chloronitrobenzene isomers are sparingly soluble in the solvent. The solidified product is collected, for example by filtration, to provide a produce enriched in meta-chloronitrobenzene.

It appears from the evidence at hand that the present process is not a conventional crystallization or recrystallization process for the reason that the chloronitrobenzene isomers are not first dissolved in the solvent and then caused to crystallize from it. Rather, the process appears to be a preferential solidification of the meta chloronitrobenzene. The molten chloronitrobenzene isomers are cooled below the melting point of meta-chloronitrobenzene, thereby causing the meta-chloronitrobenzene to preferentially solidify. A portion of the meta and other isomer or isomers in the chloronitrobenzene mixture added to the solvent are dissolved in the solvent.

Chloronitrobenzene isomer mixtures that can be purified or enriched by the process of this invention include chloronitrobenzene isomer mixtures containing at least a majority, i.e., greater than 50 weight percent, of meta-chloronitrobenzene in admixture with at least one, and usually both the ortho- and para- isomers. Desirably, the mixture contains at least about 60, preferably at least about 70 and most preferably at least about 80 weight percent of the meta isomer.

The solvent used in the solidification process described herein should be partially miscible with the chloronitrobenzene isomers at the temperature at which the isomer mixture is dispersed, i.e., the chloronitrobenzene isomers should be sparingly soluble in the solvent. If the chloronitrobenzene isomers were soluble or freely soluble in the solvent, dissolution and not solidification of the isomers would occur and thus little or no enrichment of meta- chloronitrobenzene would be realized. It is postulated that the meta-chloronitrobenzene isomer preferentially solidifies when the liquid isomer mixture is dispersed in the cooler solvent; and, that a portion of the otho, meta and para isomers are dissolved in the solvent.

The solubility of the chloronitrobenzene isomers in the solvent will, of course, depend on the solvent itself and its temperature. In practicing the present process, the isomers should be sparingly soluble in the solvent to avoid excessive solution of the meta isomer and the subsequent economically detracting steps of recovering significant quantities of the meta- isomer from the solvent. That degree of solubility, i.e., sparingly soluble, can be expressed by the amount of solvent needed to disolve one part of solute (chloronitrobenzene isomer mixture) at room temperature, i.e., about 22° C. According to Hackh's Chemical Dictionary, 3rd Edition (1944), page 787, when about 30 to about 100 parts of solvent are needed to dissolve one part of solute, the solute is said to be sparingly soluble in the solvent. Solvents of less miscibility, e.g., slightly soluble (100 to 1000 parts solvent per part of solute) can be used but their use requires quantities of solvent to compensate for their lower solubility. One skilled in the art can readily determine the solubility of the chloronitrobenzene isomer mixture to be handled at various temperatures in the solvent selected by simple experimentation and thereby determine the suitability of the solvent, or the solvent temperature needed for the degree of solubility desired.

Partially miscible liquid solvents that can be used in the present process include the lower alkylene glycols and dialkylene glycols, i.e., $C_2$–$C_6$ preferably $C_2$–$C_4$, alkylene and dialkylene glycols, and the lower alkanols, i.e., $C_1$–$C_4$ alkanols. With respect to the alkylene glycols, it is preferred that the hydroxyl substituents of the glycol are adjacent or one carbon atom removed from one another, i.e., 1,2- or 1,3-glycols. Examples of such solvents include ethylene glycol, propylene glycol (1,2-propanediol), 1,3-propanediol, 1,2-, 1,3-, and 1,4-butanediol 1,2-, 1,4-, 1,5 and 2,3-pentanediol, diethylene glycol, dipropylene glycol, methanol, ethanol, 1-propanol, 2-propanol, isopropanol, 1-butanol, 2-butanol and tertiary-butanol. Ethylene glycol, propylene glycol and methanol are preferred as the solvent.

In accordance with the present invention, the liquid chloronitrobenzene isomer mixture is dispersed in the form of small liquid droplets in the cooler solvent. These droplets solidify and are permitted to fall to the bottom of the vessel in which the solvent is contained. The dispersion can be achieved by the mode of injection into the solvent, e.g., the use of a nozzle which breaks up the isomer mixture into droplets, and/or with the use of agitation. The dispersion of droplets is maintained until solidification of the droplets. Where agitation is relied upon to both form and maintain the dispersion, the degree of agitation must be sufficient to cause formation of said dispersion of droplets in the solvent and maintain the droplets in a dispersed state until solidification is completed. Usually the liquid isomer mixture is introduced below the surface of the solvent into a zone of high agitation, e.g., near the impellor of the agitator, to form and maintain the desired dispersion.

Preferably the droplets formed have an average particle size of less than about 5 mm. and preferably less than about 2 mm., e.g., 1 mm. The size of the droplets should not be so small so that recovery by conventional recovery techniques, e.g., filtration, cannot be used; nor should the droplets be so large that the time required for solidification is extensive and/or the dispersion of such droplets is difficult to produce and maintain. Any of the techniques commonly used in the art for producing dispersions of one liquid in another can be used in the practice of the present invention. One of the more common techniques include the use of spray nozzles, of which pressure nozzles, rotating nozzles and gas-atomizing nozzles are exemplary. See, for rexample, the Chemical Engineer's Handbook, John H. Perry, Editor, 3rd Edition, 1950, pp. 1170-1175. The particle size of the droplets can be controlled in a known way by the size of the nozzle or atomizer opening and the degree of agitation.

In the practice of the herein described process, the temperature of the liquid solvent is maintained at a temperature below the melting point of meta-chloronitrobenzene (about 44° C.) and at a temperature at which the isomer mixture is sparingly soluble. Naturally, the solvent is maintained at a temperature at which it remains liquid. The preferred lower alkylene glycol solvents can be used at ordinary room temperatures, i.e., 20°-25° C. When an alkanol, such as methanol, is employed solvent temperatures substantially below room temperature are necessary to provide the desired degree of solubility.

The precise solvent temperature below 44° C. used will be a matter of economic convenience for the skilled artisan once the temperature at which the desired degree of solubility is established. Naturally, the cooler the solvent, the more energy that will be required to reach and maintain the solvent at operating temperature. Generally, ambient temperatures (if they are below 44° C.) will be used as such temperatures do not impose extraordinary heating or cooling loads on the process.

The temperature of the isomer mixture is not critical so long as the mixture is liquid. Temperatures of between about 50° C. and about 60° C. have been found particularly useful. Higher temperatures than those required to keep the isomer mixture liquid can impose unnecessary heating requirements on the process and may result in significant vaporization of the isomer mixture. Preferably, the temperature difference between the liquid isomer mixture and the liquid solvent is such that the dispersed droplets of the isomer mixture solidify in a reasonably short time. Unnecessarily wide temperature differences are not necessarily detrimental for the process and merely increase the time and energy requirements.

The ratio of solvent to isomer mixture used will depend on the degree of solubility the isomers exhibit with respect to the solvent and the amount of ortho and para isomers relative to the amount of meta isomer in the isomer mixture. Generally, the ratio of solvent to isomer mixture will range between about 1 part and about 100 parts by weight of solvent per part of isomer mixture (1:1-100:1) and, typically, between about 5 parts and about 50 parts by weight of solvent per part of isomer mixture (5:1-50:1). For most applications, a ratio of between about 5:1 and 20:1, e.g., 10:1, will be suitable. The amount of solvent used typically will be in excess of that amount required just to dissolve the amount of ortho, para, and meta isomers miscible with the solvent at the temperature of operation which dissolution results in enrichment of the meta isomer content of the isomer mixture.

After solidification, the meta enriched chloronitrobenzene solid particles are collected and separated from the solvent in any suitable manner such as filtration, centrifugation and the like. Usually the separated particles are washed with additional solvent to remove isomers contained in any adhering solvent and then dried.

The solvent used in the present process can be re-used until it becomes saturated with chloronitrobenzene isomer. Then, the isomers can be separated from the solvent by conventional techniques, e.g., distillation, and the solvent used again. In a continuous solidification process, it is contemplated that a portion of the solvent would be removed continuously from the solidification vessel. Isomer separation techniques would be applied to the isomer rich solvent and isomer lean solvent resulting therefrom recycled to the solidification vessel.

The following examples, which describe further the process of the invention, are illustrative rather than limiting. In the examples, as throughout the specification, all parts and percentages are by weight unless otherwise specified; all temperatures are degrees Centigrade unless otherwise specified. The analysis reported neglect the presence of solvent in the final products.

EXAMPLE 1

Into a 100 ml. glass beaker equipped with magnetic stirrer were charged 50 grams of ethylene glycol, to which was added 20 grams of a synthetic liquid isomer mixture composed of 5.0 percent p-chloronitrobenzene, 80.6 percent m-chloronitrobenzene and 14.4 percent o-chloronitrobenzene. The isomer mixture, at a temperature of 55° C., was injected below the surface of the stirred ethylene glycol at room temperature (about 21°-22° C.) over a five minute period through a Pasteur pipette. After stirring for 20 minutes, the resultant finely divided solid suspension was vacuum filtered through No. 50 filter paper and the recovered solids then washed sequentially with 5, 5, 10, 15 and 15 gram portions of fresh ethylene glycol. The solids where then partially dried on the filter paper by continuing the vacuum for 10 minutes. The resultant solids (16 grams) were analyzed (by gas chromotography (G.C.) on an ethylene glycol free basis and found to contain 3.3 percent p-, 87.2 percent m-, and 9.4 percent o-chloronitrobenzene.

EXAMPLE 2

In the manner of Example 1, 2 ml. of the synthetic isomer mixture described in Example 1 were added to 200 ml. of ethylene glycol to yield small solid spheres. The dispersion was stirred for about 15 minutes and then was vacuum filtered through No. 50 filter paper. The collected solids were washed two times on the filter paper with fresh ethylene glycol. These solids were pulled dry on the filter paper and analyzed by G.C. on an ethylene glycol free basis and found to contain 0.7 percent p-, 98.6 percent m- and 0.7 percent o-chloronitrobenzene.

EXAMPLE 3

To 200 grams of room temperature ethylene glycol that were rapidly stirred in a 400 ml. beaker by a magnetic stirrer were added 20 grams of the liquid isomer mixture described in Example 1 which was at 55° C. The addition was by Pasteur pipette under the surface of the glycol so that small (about 1 mm.) pellets resulted. The mixture was stirred for 15 minutes at room temperature and was then vacuum filtered through No. 50 filter paper. The solids recovered were washed sequentially on the filter with two 50 ml. portions of fresh ethylene glycol and then partially dried on the filter by pulling vacuum for about 30 minutes. The resultant solid (12.2 grams) were analyzed by G.C. on an ethylene glycol free basis and found to contain 0.7 percent p-, 98.6 percent m- and 0.7 percent o-chloronitrobenzene. The ethylene glycol phase from the filtration and washing was recovered and found to weigh 276.1 grams. 250 ml. (237.8 grams) of this ethylene glycol phase was placed in an azeotropic distillation column and the chloronitrobenzene isomers stripped from the ethylene glycol. The pot temperature of the distillation column was about 196°-198° C.

To 50 grams of room temperature ethylene glycol that were rapidly stirred in a 50 ml. beaker were added 5 grams of the aforesaid resultant solids which had been melted at 55° C. The addition was by Pasteur pipette under the surface of the glycol so that small droplets resulted. After stirring for 15 minutes, the resultant solids were collected on No. 50 filter paper by vacuum filtration. The recovered solids were washed sequentially with 5, 5, 20, and 20 gram portions of fresh ethylene glycol. The resultant solids (2.5 grams) were analyzed by G.C. on an ethylene glycol free basis and found to contain 0.4 percent p-, 99.5 percent m- and 0.1 percent o-chloronitrobenzene.

EXAMPLE 4

To 50 grams of room temperature propylene glycol, which were rapidly stirred in a beaker, were added 5 grams of the liquid isomer mixture of Example 1, which were heated to 55° C. The addition was by Pasteur pipette under the surface of the propylene glycol so that small droplets resulted. After a few minutes of stirring, a dispersion of fine solids appeared which were collected and washed with fresh propylene glycol. The resultant wet solids (5.1 grams) were analyzed by G.C. on a propylene glycol free basis and found to contain 1.0 percent p-, 97.6 percent m- and 1.3 percent o-chloronitrobenzene.

Examples 1-4 show that the lower alkylene glycols can be used to enrich the meta content of a chloronitrobenzene isomer mixture. The examples show further that purification occurs better with higher ratios of solvent to isomer mixtures and that repeated solidifications of enriched isomer mixture improves further the meta isomer content.

EXAMPLE 5

To compare liquid-liquid extration with the solidification process of the invention, 2.7 grams of the isomer mixture described in Example 1, were shaken with 27 grams of ethylene glycol at 55° C. until equilibrium was attained, i.e., about ½ to 1 minute. The resultant mixture was set in a 55° C. oven overnight to allow the phases to separate. The resultant chloronitrobenzene phase was analyzed by G.C. and found to contain 4.5 percent p-, 83.4 percent m- and 12.2 percent o-chloronitrobenzene. This example shows that there was little enrichment of the meta isomer by the aforesaid extraction technique.

EXAMPLE 6

Each of the following runs were conducted as follows:

Into a glass beaker equipped with a magnetic stirrer were charged 50 grams of ethylene glycol. To the rapidly stirred ethylene glycol were added 5 grams of synthetic chloronitrobenzene isomer mixture consisting of 3.6 percent p-chloronitrobenzene, 86.0 percent m-chloronitrobenzene and 10.4 percent o-chloronitrobenzene, under the specified conditions described in the following enumerated "Runs".

Run 1 isomer mixture at 55° C. added to ethylene glycol at room temperature to yield 3.5 grams of solid which analyzed 1.2 percent p-, 97.5 percent m-and 1.3 percent o-chloronitrobenzene.

Run 2 isomer mixture at 55° C. added to ethylene glycol at 55° C. to yield a two phase system which was stirred for five minutes and then allowed to cool to room temperature; no solid was seen; the oil phase (3.0 grams) analyzed 3.7 percent p-, 87.9 percent m- and 8.4 percent o-chloronitrobenzene.

Run 3 Run 2 repeated except stirring was continued overnight as the mixture cooled; the mixture was then cooled to 15° C.; no solid was seen; the oil phase analyzed 3.7 percent p-, 87.8 percent m- and 8.6 percent o-chloronitrobenzene.

Run 4 isomer mixture at 55° C. added to ethylene glycol at 100° C. to yield a single phase, which was cooled with stirring to 55° C. where a second oil phase formed; the cooling was continued to room temperature with stirring; the oil phase analyzed 3.7 percent p-, 86.0 percent m- and 10.3 percent o-chloronitrobenzene.

Run 5 Run 4 was repeated except that cooling was extended with stirring to about 0° C. where solids formed; the mixture was warmed to room temperature and the solid (3.3 grams) was collected; it analyzed 0.8 percent p- and 99.2 percent m-chloronitrobenzene with only a trace of o-chloronitrobenzene.

The data of Runs 1-5 of Example 6 show that the purification achieved by the process of the present invention is not by recrystallization but is achieved in the process of solidifying the meta-chloronitrobenzene.

EXAMPLE 7

Each of the following Runs were conducted as follows:

Into a glass beaker equipped with a magnetic stirrer were charged 50 grams of methanol. To the rapidly stirred methanol were added 5 grams of the synthetic liquid isomer mixture of Example 6, under the specified conditions described in the following enumerated "Runs".

Run 1 isomer mixture at 55° C. added to methanol at room temperature to form a solution which was cooled with stirring to −30° C., solid formation occurred and precipitated; 2.4 grams of solid were collected by filtration at −30° C.; it analyzed 1.5 percent p- and 98.5 percent m-chloronitrobenzene, with only a trace of o-chloronitrobenzene.

Run 2 isomer mixture at 55° C. added to methanol at −40° C., solid formed immediately; solid filtered at −40° C.; it analyzed 2.7 percent p-, 93.8 percent m- and 3.5 percent o-chloronitrobenzene.

Run 3 Run 7 repeated with methanol at −65° C.; 4.1 grams of filtered solids were collected; they analyzed 2.2 percent p-, 95.4 percent m- and 2.4 percent o-chloronitrobenzene.

The data of Runs 1–3 of Example 7 show that recrystallization from methanol yields purified meta-chloronitrobenzene (Run 1); but, that at low temperatures where solubility of the isomers is low, significant purification is achieved by solidification without the need to first dissolve and then precipitate the isomers from the solvent.

EXAMPLE 8

Into a glass beaker equipped with a magnetic stirrer were charged 50 grams of water. To the rapidly stirred water, which was at room temperature, were added 5 grams of the liquid (55° C.) isomer mixture described in Example 6. Solid formed at the bottom of the beaker. 5 grams of solid were collected and when analyzed found to contain 3.7 percent p-, 86.1 percent m- and 10.3 percent o-chloronitrobenzene, i.e., no apparent isomer separation.

In the above examples, the analysis of chloronitrobenzene isomers was carried out by gas chromatography using a 12 foot by ⅛ inch stainless steel column packed with Siponate DS-10 on Chromosorb W 100/120 at 200° C. with the injection port at 180° C., the detector at 230° C., and a helium flow at 25 cc/min.

While the above examples are directed to batch processes, it is obvious that, if desired, the process of the invention can be adapted to operate in a continuous fashion. Likewise, the exemplified processes can be varied by substituting isomer mixtures or solvents described above, and/or by varying temperatures and proportions within the scope of the disclosure.

What is claimed is:

1. A process for enriching the meta-chloronitrobenzene content of a chloronitrobenzene isomer mixture, which comprises dispersing a liquid chloronitrobenzene isomer mixture containing meta-chloronitrobenzene as the major isomer into a partially miscible solvent having a temperature below the melting point of meta-chloronitrobenzene, said solvent and its temperature being selected so that the isomer mixture is sparingly soluble in said solvent, the weight ratio of said solvent to said isomer mixture being between about 1:1 and about 100:1, thereby forming a particulate chloronitrobenzene solid enriched in meta-chloronitrobenzene content.

2. The process of claim 1 wherein the weight ratio of solvent to isomer mixture is between about 5:1 and 20:1.

3. The process of claim 1 wherein the solvent is a $C_2$–$C_6$ alkylene glycol.

4. The process of claim 3 wherein the solvent is ethylene glycol or propylene glycol.

5. The process of claim 4 wherein the liquid isomer mixture is at a temperature of between about 50° C. and about 60° C. and the solvent is at about room temperature.

6. The process of claim 1 wherein the isomer mixture contains at least 70 weight percent meta-chloronitrobenzene.

7. A process for enriching the meta-chloronitrobenzene content of a chloronitrobenzene isomer mixture, which comprises dispersing a liquid chloronitrobenzene isomer mixture containing meta-chloronitrobenzene as the major isomer into a lower alkanol solvent having from 1 to 4 carbon atoms, said solvent having a temperature below the melting point of meta-chloronitrobenzene, said temperature being selected so that the isomer mixture is sparingly soluble in said solvent, the weight ratio of said solvent to said isomer mixture being between about 1:1 and about 100:1, thereby forming a particulate chloronitrobenzene solid enriched in meta-chloronitrobenzene content.

8. The process of claim 7 wherein the solvent is methanol.

9. The process of claim 5 wherein the isomer mixture contains at least 80 weight percent meta-chloronitrobenzene.

* * * * *